United States Patent
Hunt et al.

(10) Patent No.: US 10,274,310 B2
(45) Date of Patent: Apr. 30, 2019

(54) SURFACE SENSING SYSTEMS AND METHODS FOR IMAGING A SCANNED SURFACE OF A SAMPLE VIA SUM-FREQUENCY VIBRATIONAL SPECTROSCOPY

(71) Applicants: The Boeing Company, Chicago, IL (US); FemtoMetrix, Inc., Irvine, CA (US)

(72) Inventors: Jeffrey H. Hunt, Thousand Oaks, CA (US); Jianing Shi, Sunnyvale, CA (US); John Paul Changala, Tustin, CA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/388,743

(22) Filed: Dec. 22, 2016

(65) Prior Publication Data

US 2018/0180404 A1   Jun. 28, 2018

(51) Int. Cl.
*G01B 11/24* (2006.01)
*G01J 3/10* (2006.01)
(Continued)

(52) U.S. Cl.
CPC ............... *G01B 11/24* (2013.01); *G01J 3/10* (2013.01); *G01J 3/108* (2013.01); *G01J 3/44* (2013.01);
(Continued)

(58) Field of Classification Search
CPC ............... G01B 11/24; G01N 21/1717; G01N 2021/1725; G01N 21/9501;
(Continued)

(56) References Cited

U.S. PATENT DOCUMENTS 4,652,757 A * 3/1987 Carver ............... G01N 21/1717
                                                  250/338.1
5,270,546 A * 12/1993 Jamroz .............. G01N 21/4738
                                                  250/340
(Continued)

OTHER PUBLICATIONS

Zhuang, "Nano-imaging with Storm," NIH-PA Author Manuscript, Nat Photonics, 3(7), pp. 365-367, 2009.
(Continued)

*Primary Examiner* — Isiaka O Akanbi
(74) *Attorney, Agent, or Firm* — Dascenzo Intellectual Property Law, P.C.

(57) ABSTRACT

Surface sensing systems and methods for imaging a scanned surface of a sample via sum-frequency vibrational spectroscopy are disclosed herein. The systems include a sample holder, a visible light source configured to direct a visible light beam incident upon a sampled location of the scanned surface and a tunable IR source configured to direct a tunable IR beam coincident with the visible light beam upon the sampled location. The systems also include a scanning structure configured to scan the visible light beam and the tunable IR beam across the scanned surface, and a light filter configured to receive an emitted beam from the scanned surface and to filter the emitted beam to generate a filtered light beam. The systems further include a light detection system configured to receive the filtered light beam, and an alignment structure. The methods include methods of operating the systems.

13 Claims, 4 Drawing Sheets

(51) Int. Cl.
  *G01J 3/44* (2006.01)
  *G01N 21/63* (2006.01)
  *G01N 21/65* (2006.01)
(52) U.S. Cl.
  CPC ........... *G01N 21/636* (2013.01); *G01N 21/65* (2013.01); *G01J 2003/102* (2013.01); *G01N 2021/638* (2013.01); *G01N 2021/655* (2013.01); *G01N 2201/103* (2013.01); *G01N 2201/105* (2013.01)
(58) Field of Classification Search
  CPC ............... G01N 21/8422; G01N 21/94; G01N 21/3563; G01R 31/2656
  USPC .......................... 356/601–624, 369, 432, 492
  See application file for complete search history.

(56) References Cited

U.S. PATENT DOCUMENTS

| | | | |
|---|---|---|---|
| 5,623,341 A | 4/1997 | Hunt | |
| 5,973,778 A | 10/1999 | Hunt | |
| 6,781,686 B2 | 8/2004 | Hunt | |
| 6,788,405 B2 | 9/2004 | Hunt | |
| 6,795,175 B2 | 9/2004 | Hunt | |
| 6,798,502 B2 | 9/2004 | Hunt | |
| 6,819,844 B2 | 11/2004 | Hunt | |
| 6,882,414 B2 | 4/2005 | Hunt | |
| 7,212,288 B2* | 5/2007 | Opsal | G01N 21/1717 356/432 |
| 7,304,305 B2 | 12/2007 | Hunt | |
| 2007/0008501 A1* | 1/2007 | Yamazaki | H04N 9/3129 353/97 |
| 2007/0263226 A1* | 11/2007 | Kurtz | A61B 5/0059 356/492 |
| 2008/0007733 A1* | 1/2008 | Marks | A61B 5/0066 356/477 |
| 2009/0114805 A1* | 5/2009 | Csutak | G01N 21/636 250/269.1 |
| 2016/0153918 A1* | 6/2016 | Kim | G01N 21/956 356/239.3 |

OTHER PUBLICATIONS

Huang et al., "Three-dimensional Super-resolution Imaging by Stochastic Optical Reconstruction Microscopy," NIH-PA Author Manuscript, Science, 319(5864), pp. 810-813, Feb. 8, 2008.

Guyot-Sionnest et al. "Sum-Frequency Vibrational Spectroscopy of a Langmuir Film: Study of Molecular Orientation of a Two-Dimensional System," The American Physical Society, Physical Review Letters, vol. 59, No. 14, Oct. 5, 1987.

* cited by examiner

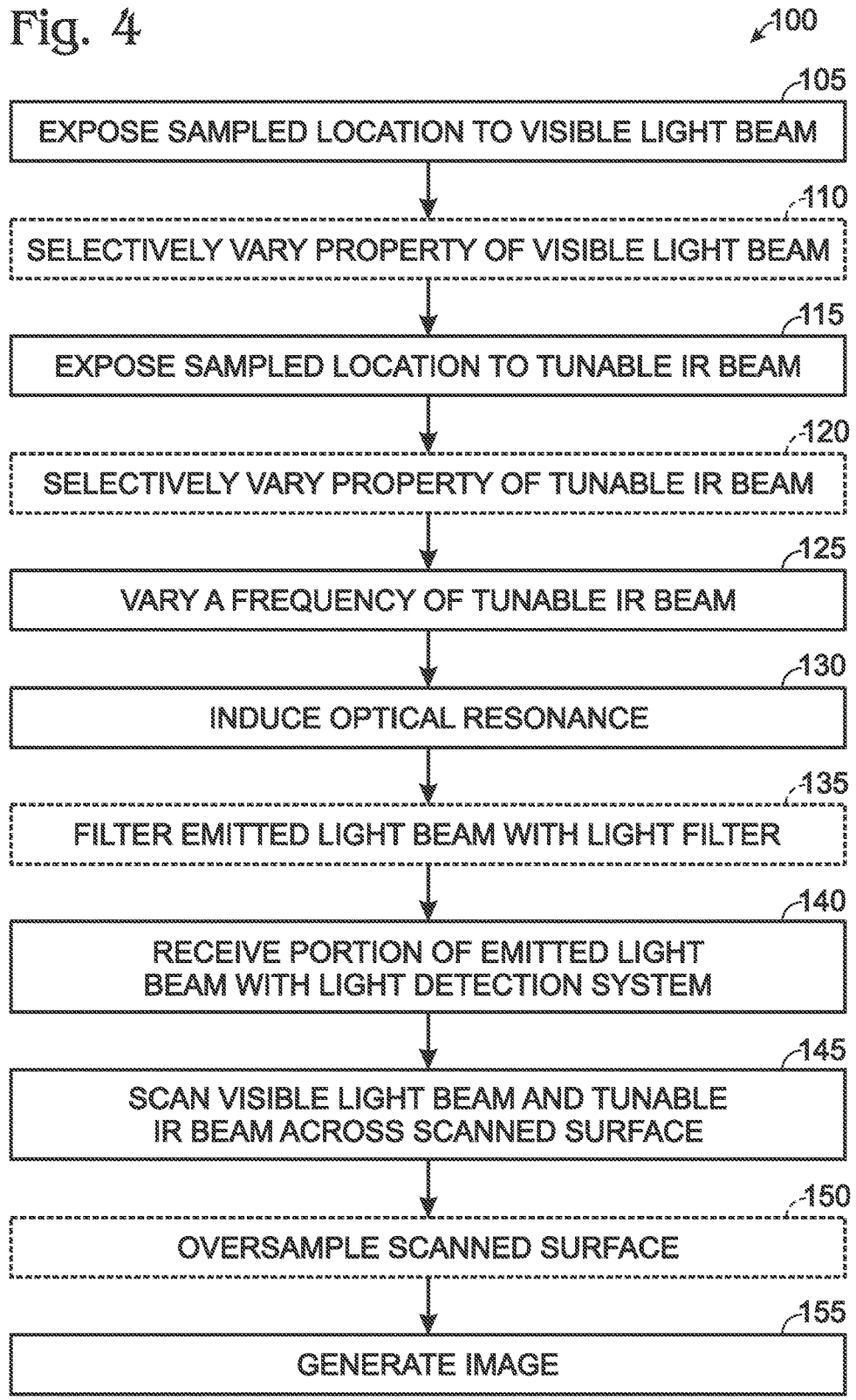

SURFACE SENSING SYSTEMS AND METHODS FOR IMAGING A SCANNED SURFACE OF A SAMPLE VIA SUM-FREQUENCY VIBRATIONAL SPECTROSCOPY

FIELD

The present disclosure relates generally to systems and methods for imaging a scanned surface of a sample and more particularly to systems and methods that scan both a visible light beam and a tunable infrared beam across the scanned surface to characterize the scanned surface.

BACKGROUND

Non-linear optical spectroscopy may be utilized to detect the presence of, to identify, and/or to visualize, one or more materials and/or objects on a surface. However, the spatial resolution of such non-linear optical spectroscopy techniques generally is limited by the diffraction limit as governed by the wavelength of light and/or the Nyquist sampling theorem. This diffraction limit is on the order of 1 micrometer, and it may be desirable to visualize objects that are several orders of magnitude smaller (e.g., on the order of 1 nm).

Detecting, identifying, and/or visualizing objects significantly smaller than 1 micrometer generally requires that electron-scattering techniques be utilized. However, electron-scattering techniques must be performed in ultrahigh vacuum environments, thus limiting their utility for many industrial applications. As an example, it may be costly, time-consuming, and/or simply not feasible to establish an ultrahigh vacuum environment around certain objects, thereby precluding scanning of these objects via electron-scattering techniques. In addition, electrons may alter the physical state of the surface instead of being purely, or largely, diagnostic in nature.

Alternatively, and in certain systems, such as biological systems, a photoactivatable label, or tag, may be added to known locations within an object to be visualized. In such a configuration, the photoactivatable label may be "turned on" or "turned off," thereby providing additional contrast between the object to be visualized and the background, or noise, that inherently is present, preventing bleeding and/or contamination between adjacent elements of the object, and/or reducing signal aliasing. While such photoactivatable labels may improve resolution in certain systems, they may be difficult to add to and/or may contaminate other systems.

As discussed above, known systems and methods for detecting, identifying, and/or visualizing objects on a surface may not be amenable to all systems. Thus there exists a need for improved surface sensing systems and methods for imaging a scanned surface of a sample.

SUMMARY

Surface sensing systems and methods for imaging a scanned surface of a sample via sum-frequency vibrational spectroscopy are disclosed herein. The systems include a sample holder, a visible light source configured to direct a visible light beam incident upon a sampled location of the scanned surface and a tunable IR source configured to direct a tunable IR beam coincident with the visible light beam upon the sampled location. The tunable IR source is configured to selectively vary, or scan, a wavelength of the tunable IR beam, thereby permitting the tunable IR beam to selectively induce resonance within an imaged structure that is positioned on the scanned surface. The systems also include a scanning structure configured to scan the visible light beam and the tunable IR beam across the scanned surface, and a light filter configured to receive an emitted beam from the scanned surface and to filter the emitted beam to generate a filtered light beam. The emitted light beam includes a sum frequency signal, which propagates at an angle, between the specularly reflected visible light beam and the tunable IR beam, and is emitted from the scanned surface responsive to both the visible light beam and the tunable IR beam being incident on the scanned surface. The systems further include a light detection system configured to receive the filtered light beam, and an alignment structure.

The methods include methods of imaging the scanned surface of the sample. The methods include directing the visible light beam and the tunable IR beam coincident upon the sampled location of the scanned surface. The methods also include tuning the tunable IR beam to induce optical resonance within an imaged structure that extends at least partially within the sampled location of the scanned surface. Tuning the tunable IR beam also may be referred to herein as varying the wavelength of the tunable IR beam and/or as scanning a spectrum of the tunable IR beam. The methods further include receiving at least a portion of the emitted light beam from the sampled location of the scanned surface with a light detection system and scanning the visible light beam and the tunable IR beam across the scanned portion of the scanned surface. The methods also include generating an image of the scanned portion of the scanned surface based, at least in part, on the receiving and on the scanning.

BRIEF DESCRIPTION OF THE DRAWINGS

FIG. 4 is a flowchart depicting methods, according to the present disclosure, for imaging a scanned surface of a sample.

DESCRIPTION

Figure 1:
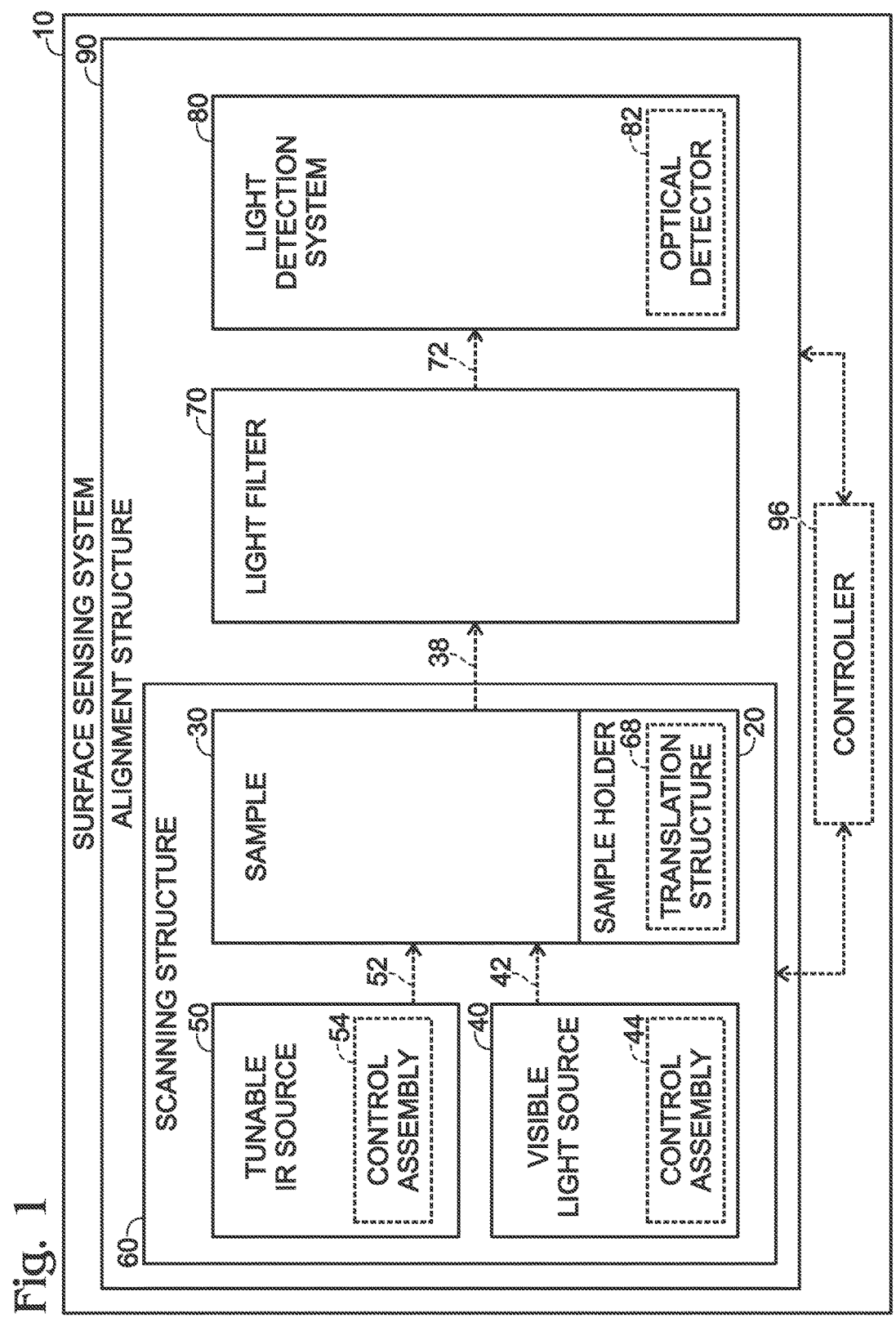
FIG. 1 is a functional block diagram illustrating examples of a surface sensing system according to the present disclosure.

FIGS. 1-4 provide illustrative, non-exclusive examples of surface sensing systems 10 and/or of methods 100, according to the present disclosure. Elements that serve a similar, or at least substantially similar, purpose are labeled with like numbers in each of FIGS. 1-4, and these elements may not be discussed in detail herein with reference to each of FIGS. 1-4. Similarly, all elements may not be labeled in each of FIGS. 1-4, but reference numerals associated therewith may be utilized herein for consistency. Elements, components, and/or features that are discussed herein with reference to one or more of FIGS. 1-4 may be included in and/or utilized with any of FIGS. 1-4 without departing from the scope of the present disclosure.

In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a given example without departing from the scope of the present disclosure.

Figure 2:
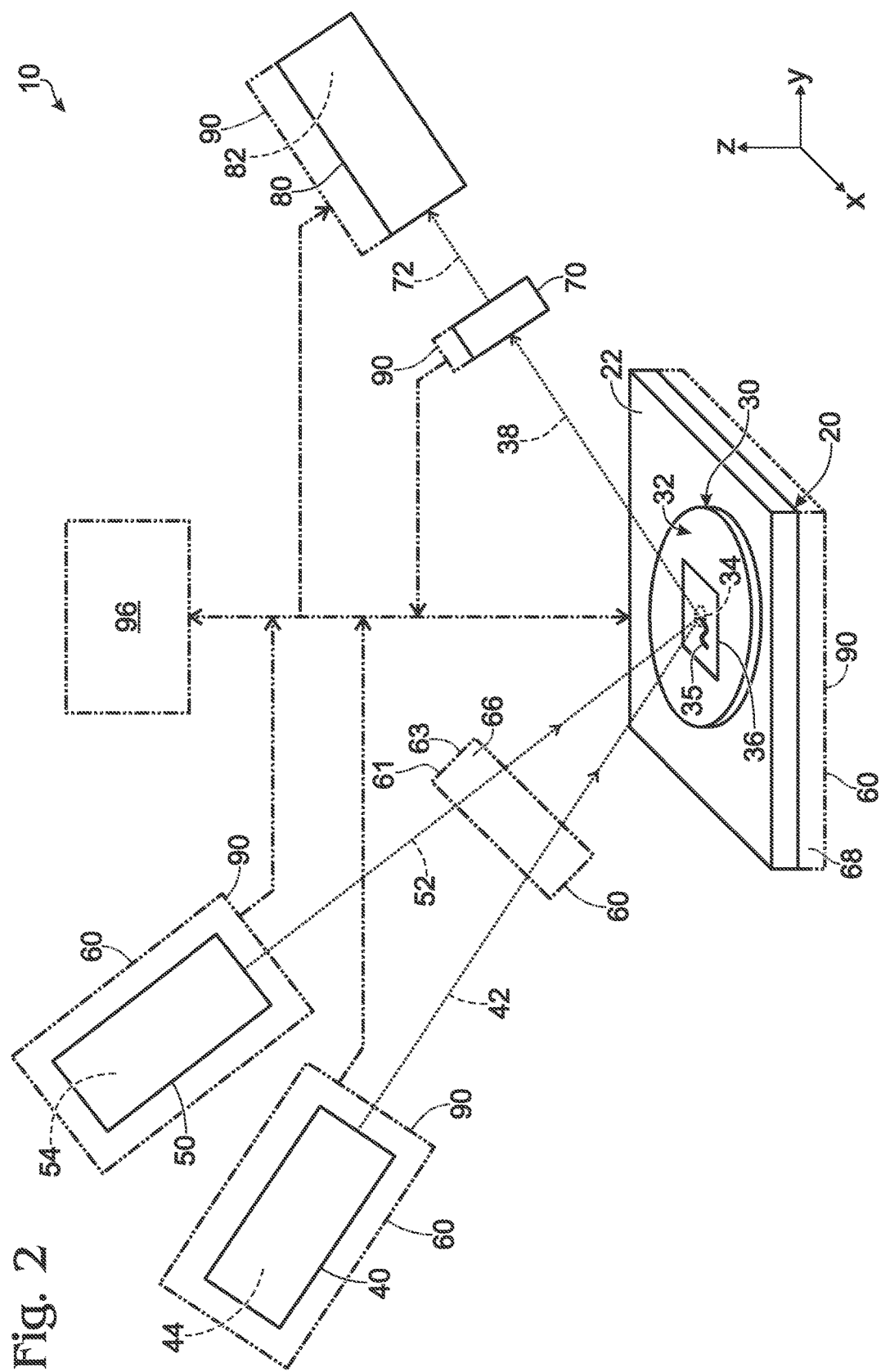
FIG. 2 is a less schematic illustration of a more specific example of a surface sensing system according to the present disclosure.
Figure 3:
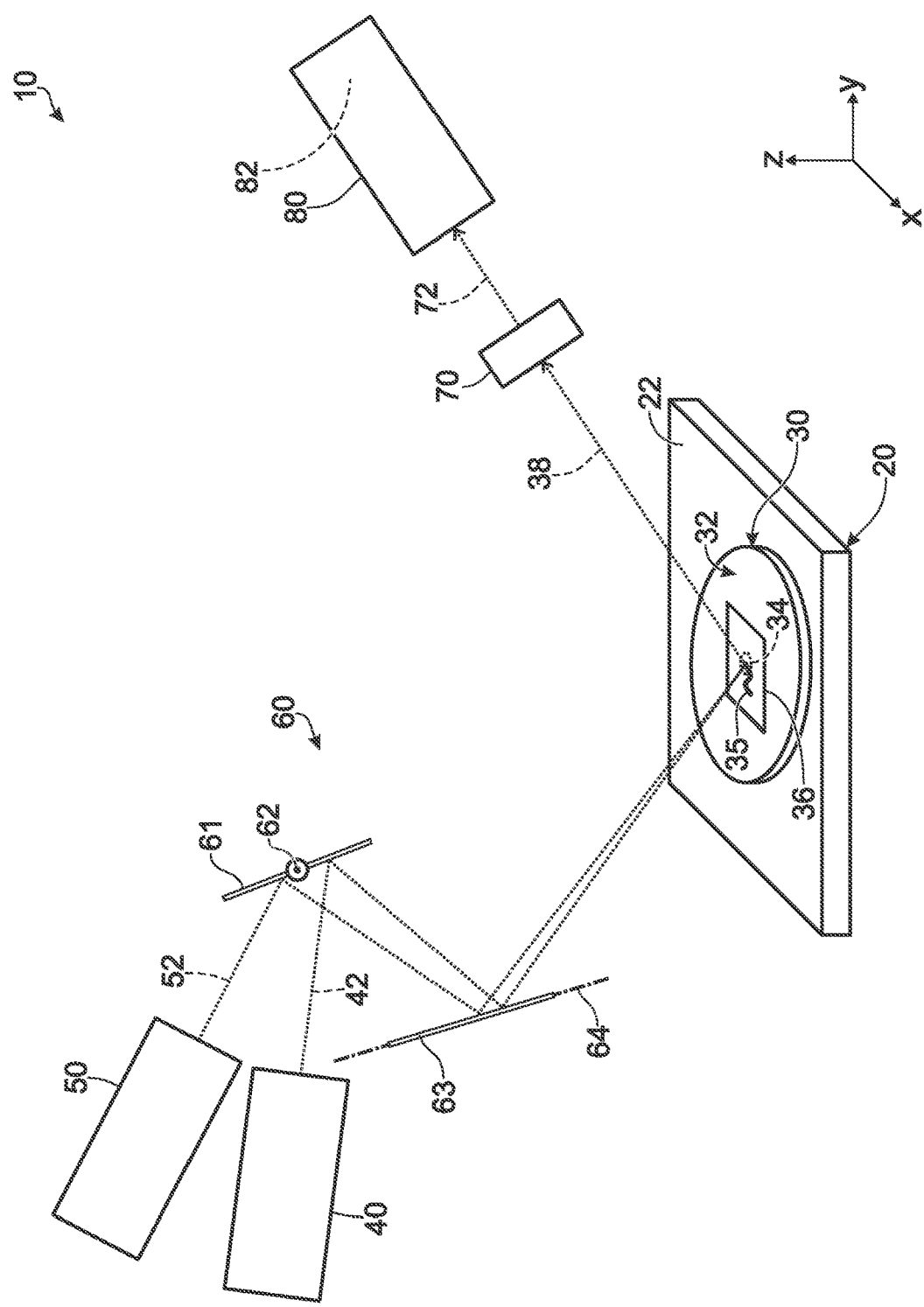
FIG. 3 is another a less schematic illustration of a more specific example of a surface sensing system according to the present disclosure.

FIG. 1 is a functional block diagram illustrating examples of a surface sensing system 10 according to the present disclosure, while FIGS. 2-3 are less schematic illustrations of more specific examples of a surface sensing system 10 according to the present disclosure. Surface sensing systems 10 also may be referred to herein as systems 10 and are configured to image a scanned surface 32 of a sample 30.

As illustrated in FIGS. 1-3, systems 10 include a sample holder 20 including a support surface 22, which is configured to support a sample 30. Systems 10 also include a visible light source 40, which is configured to direct a visible light beam 42 incident upon a sampled location 34 on a scanned surface 32; and a tunable infrared (IR) source 50, which is configured to direct a tunable IR beam 52 incident upon sampled location 34 of scanned surface 32. Responsive to receipt of both visible light beam 42 and tunable IR beam 52, sampled location 34 of scanned surface 32 produces, generates, and/or emits an emitted light beam 38. Emitted light beam 38 is a sum frequency signal between visible light beam 42 and tunable IR beam 52.

Systems 10 further include a scanning structure 60. Scanning structure 60 is configured to scan visible light beam 42 and tunable IR beam 52 across scanned surface 32, such as to selectively change, or vary, a portion of scanned surface 32 that defines sampled location 34. This may include scanning both the visible light beam and the tunable IR beam within a scanned portion, or region, 36 of scanned surface 32 to permit system 10 to create and/or generate an image of scanned portion 36 of scanned surface 32.

Systems 10 also include a light filter 70. Light filter 70 is configured to receive emitted light beam 38 from sampled location 34 of scanned surface 32 and to filter emitted light beam 38 to produce and/or generate a filtered light beam 72. Filtered light beam 72 is received by a light detection system 80, which may measure and/or quantify a frequency, wavelength, intensity, and/or polarization of filtered emitted light beam 38.

System 10 further includes an alignment structure 90. Alignment structure 90 is configured to operatively align two or more components of system 10, such as sample holder 20, visible light source 40, tunable IR source 50, light filter 70, and/or light detection system 80. This may include operative alignment of the two or more components of system 10 such that visible light beam 42 and tunable IR beam 52 are coincident upon sampled location 34, such that emitted light beam 38 is received by light filter 70, and/or such that filtered light beam 72 is received by light detection system 80. This is illustrated in FIGS. 2-3, with FIG. 1 simply being utilized to more generally illustrate the interconnection among the various components of surface sensing system 10.

During operation of system 10 and as discussed in more detail herein with reference to methods 100 of FIG. 4, visible light source 40 and tunable IR source 50 may direct visible light beam 42 and tunable IR beam 52, respectively, onto, or incident upon, sampled location 34 of scanned surface 32. Responsive to receipt of both visible light beam 42 and tunable IR beam 52, sampled location 34 may produce, generate, and/or emit emitted light beam 38. Emitted light beam 38 may be filtered by light filter 70 to produce and/or generate filtered light beam 72, which may be received by light detection system 80. Light detection system 80 then may quantify at least one property of filtered light beam 72.

Then, tunable IR source 50 may be tuned, such as by varying a wavelength, a frequency, or both the wavelength and the frequency of tunable IR beam 52, to a wavelength and/or frequency that produces and/or generates optical resonance within an imaged structure 35 that extends at least partially, or even completely, within sampled location 34 of scanned surface 32. Tunable IR source 50 may be configured to selectively vary, or scan, the wavelength and/or the frequency of the tunable IR beam 52, with this selective variation being utilized to selectively induce resonance within the imaged structure. This resonance causes the imaged structure to absorb the tunable IR beam 52 that is incident thereupon. In contrast, a remainder of sampled location 34 and/or of scanned surface 32, which is not in resonance with tunable IR beam 52, does not absorb tunable IR beam 52. Thus, the optical resonance within imaged structure 35 provides optical contrast between imaged structure 35 and scanned surface 32 (e.g. a background). Subsequently, visible light beam 42 and tunable IR beam 52 may be scanned across scanned surface 32 to produce and/or generate an image of scanned portion 36 of scanned surface 32. This image may correlate and/or display a value of at least one property of filtered light beam 72 as a function of location within scanned portion 36 of scanned surface 32.

Prior art systems rely upon a photoactive label and/or tag to distinguish an imaged structure from a remainder of a scanned surface. However, systems 10, which are disclosed herein, utilize tunable IR beam 52 to induce optical resonance within chemical compounds that are native to, or naturally present within, imaged structure 35. As such, systems 10 may permit imaging of imaged structure 35 and/or may provide optical contrast between imaged structure 35 and a background, or remainder, of scanned surface 32 without the need to introduce a foreign material, or contaminant, such as the photoactive label, into sample 30. Such a configuration may permit systems 10, which are disclosed herein, to image samples 30 that may be damaged, altered, and/or otherwise affected through introduction of a photoactive label.

Subsequent to collection of the above-described image, system 10 may be utilized to collect a plurality, or sequence, of additional, or subsequent, images of scanned portion 36 of scanned surface 32. This process, which is discussed in more detail herein with reference to methods 10, may be referred to herein as oversampling, and may be utilized to produce and/or generate a super-resolution image of imaged structure 35. As used herein, the phrase "super-resolution image" includes an image, such as of imaged structure 35, that has a higher resolution that what may be obtained from a single observance, or image, of imaged structure 35. As used herein, the word "oversampling" may refer to collection of the plurality, or sequence, of images, and each of these images also may be referred to herein as an "undersampled" image.

As an example, a single scan of scanned portion 36 of scanned surface 32 by systems 10 may produce and/or generate an image with a resolution of approximately 1 micrometer due to the diffraction-limited nature of optical imaging techniques. Systems 10 may be able to resolve, or focus upon, an imaged structure 35 that is 1 micrometer in size, or larger, when imaged structure 35 is imaged by a single scan of scanned portion 36 of scanned surface 32. A minimum spot size of visible light beam 42 and/or of tunable IR beam 52 on scanned surface 32 is limited, approximately, to the wavelength of the corresponding beam due to diffraction effects. Thus, systems 10 generally cannot resolve imaged structures 35 that are less than 1 micrometer in size in a single scan.

However, the oversampling may permit systems 10 to produce super-resolution images that resolve imaged structure 35 to a resolution of less than 1 micrometer. As examples, the super-resolution images may resolve imaged structure 35 to a resolution of less than 500 nanometers, less than 250 nanometers, less than 200 nanometers, less than 100 nanometers, less than 75 nanometers, less than 50 nanometers, less than 25 nanometers, or less than 10 nanometers. In general, the resolution of the super-resolution image may be improved by increasing the number of images that are combined to generate the super-resolution image and/or by tuning tunable IR beam 52.

Activating non-linear resonance of naturally occurring surface features, via systems 10 and/or methods 100, may provide improved surface sensing and enables super-resolution images to be generated in the context of a non-linear optical system. Prior art systems instead rely upon photoactive tags and/or labels to provide the contrast needed for collection of super-resolution images; however, and as discussed, such photoactive tags and/or labels modify the system being imaged and therefore may not be utilized in certain circumstances.

This may enable second order surface sensing (e.g., via the non-linear optical system) as well as third order material, interface, structure, and compositional sensing. Stated another way, systems 10 and/or methods 100 are configured to utilize non-linear optical techniques to image a surface, such as scanned surface 32, and/or to characterize the surface based upon a second and/or a third order susceptibility of the surface. Examples of the second order surface sensing include second harmonic generation, sum-frequency generation, and/or difference-frequency generation. Examples of third order sensing include stimulated Raman scattering, stimulated Brillion scattering, 4-wave mixing, and optical phase conjugation. The response of the surface to these second and third order surface sensing techniques is governed by susceptibility, which becomes a second or third order susceptibility tensor for second or third order sensing techniques, respectively.

Visible light source 40 may include any suitable structure that may be adapted, configured, designed, and/or constructed to generate visible light beam 42 and/or to direct visible light beam 42 incident upon sampled location 34 of scanned surface 32. As examples, visible light source 40 may include one or more of a pulsed laser system, a solid state laser, and/or a neodymium YAG laser. When visible light source 40 includes the neodymium YAG laser, the neodymium YAG laser may be frequency doubled, such as to a wavelength of approximately 0.532 micrometers, so that visible light beam 42 is within the visible light spectrum.

Visible light beam 42 may have any suitable frequency, wavelength, intensity, and/or polarization that may interact with tunable IR beam 52, within sampled location 34, to produce and/or generate emitted light beam 38. As examples, visible light beam 42 may have a wavelength, a primary wavelength, and/or an average wavelength of at least 0.1 micrometer, at least 0.2 micrometers, at least 0.3 micrometers, at least 0.4 micrometers, at least 0.5 micrometers, at least 0.6 micrometers, at most 1 micrometer, at most 0.9 micrometers, at most 0.8 micrometers, at most 0.7 micrometers, at most 0.6 micrometers, and/or at most 0.5 micrometers. It is within the scope of the present disclosure that visible light beam 42 may have a fixed, or at least substantially fixed, wavelength and/or output spectrum, at least during collection of a given image of sample 30. Visible light beam 42 may have a frequency that is within, or near, the visible light spectrum, and a frequency, wavelength, bandwidth, and/or intensity of visible light beam 42 may vary by less than 5%, less than 2.5%, less than 1%, and/or less than 0.1%, at least during collection of the given image of sample 30. Such visible light beams 42 may generate emitted light beams 38 that are in the visible range, such as with a wavelength of about 390-800 nm. In a practical sense, optical detector 82 may be more efficient and/or effective at detecting visible light when compared to lower or higher frequency light, and this improvement in efficiency may be especially important when utilizing system 10 to detect a few, or even a single, photon via optical detector 82.

As illustrated in dashed lines in FIGS. 1-3, visible light source 40 also may include a visible light source control assembly 44. Visible light source control assembly 44, when present, may be adapted, configured, designed, and/or constructed to vary one or more of an intensity of visible light beam 42, a polarization of visible light beam 42, a wavelength of visible light beam 42, and/or a bandwidth of visible light beam 42 such that visible light beam 42 interacts with tunable IR beam 32, within sampled location 34, to produce and/or generate emitted light beam 38 that is the sum frequency signal between visible light beam 42 and tunable IR beam 32.

Tunable IR source 50 may include any suitable structure that may be adapted, configured, designed, and/or constructed to generate tunable IR beam 52 and/or to direct tunable IR beam 52 incident upon sampled location 34 of scanned surface 32. As examples, tunable IR source 50 may include an optical parametric oscillator and/or a lithium niobate ($LiNbO_3$) crystal laser.

Tunable IR beam 52 may have any suitable frequency, wavelength, intensity, and/or polarization that may interact with visible light beam 42, within sampled location 34, to produce and/or generate emitted light beam 38. In addition, tunable IR source 50 may be configured to selectively tune and/or vary the frequency of tunable IR beam 52, such as to permit the tunable IR beam to induce optical resonance within the imaged structure. Stated another way, tunable IR source 50 may have a selectively variable output wavelength and/or a selectively variable output spectrum. As examples, tunable IR beam 52 may have, or be tuned to, a wavelength, a primary wavelength, and/or an average wavelength of at least 0.7 micrometers, at least 0.8 micrometers, at least 0.9 micrometers, at least 1 micrometer, at least 10 micrometers, at least 25 micrometers, at least 50 micrometers, at least 100 micrometers, at least 200 micrometers, at least 300 micrometers, at least 400 micrometers, at least 500 micrometers, at least 600 micrometers, at least 700 micrometers, at most 1000 micrometers, at most 900 micrometers, at most 800 micrometers, at most 700 micrometers, at most 600 micrometers, at most 500 micrometers, at most 400 micrometers, at most 300 micrometers, at most 200 micrometers, or at most 100 micrometers.

As illustrated in dashed lines in FIGS. 1-3, tunable IR source 50 also may include a tunable IR source control assembly 54. Tunable IR source control assembly 54, when present, may be adapted, configured, designed, and/or constructed to vary one or more of an intensity of tunable IR beam 52, a polarization of tunable IR beam 52, a wavelength of tunable IR beam 52, and/or a bandwidth of tunable IR beam 52. The polarization of tunable IR beam 52 may be varied, via tunable IR source control assembly 54, to emphasize, or deemphasize, various spectral features, such as portions of imaged structure 35 that may be aligned with, may be misaligned with, may resonate in a plane that is aligned with, and/or may resonate in a plane that is misaligned with the polarization of the tunable IR beam. This may provide additional information regarding alignment and/or conformation of molecules on scanned surface 32.

Scanning structure 60 may include any suitable structure that may be adapted, configured, designed, and/or constructed to scan visible light beam 42 and tunable IR beam 52 across scanned surface 32 and/or within scanned portion 36 of scanned surface 32, such as to selectively vary the portion of scanned surface 32 that defines sampled location 34 (e.g., the portion of scanned surface 32 upon which visible light beam 42 and tunable IR beam 52 are coincident). In general, scanning structure 60 maintains visible light beam 42 and tunable IR beam 52 coincident upon sampled location 34 during the scanning process. Scanning structure 60 may scan visible light beam 42 and tunable IR beam 52 across scanned surface 32 in any suitable manner. As an example, scanning structure 60 may raster scan visible light beam 42 and tunable IR beam 52 across scanned surface 32.

As an example, scanning structure 60 may include a motorized scanning structure 60 configured to selectively and/or automatically scan the visible light beam and the tunable IR beam across scanned surface 32. As another example, scanning structure 60 may include a sample holder translation structure 68 configured to operatively translate sample holder 20 relative to both visible light beam 42 and tunable IR beam 52. As yet another example, scanning structure 60 may include an optic steerer 66. Examples of optic steerer 66 include an electrooptic steerer and an acoustooptic steerer.

As another example, and as perhaps best illustrated in FIG. 3, scanning structure 60 may include a first mirror 61 and a second mirror 63. First mirror 61 may be configured to receive visible light beam 42 from visible light source 40 and also to receive tunable IR beam 52 from tunable IR source 50. First mirror 61 further may be configured to reflect visible light beam 42 and tunable IR beam 52 and also to pivot about a first axis 62 and thereby to scan both visible light beam 42 and tunable IR beam 52 across scanned surface 32 in a first direction. Second mirror 63 may be configured to receive visible light beam 42 and tunable IR beam 52 from first mirror 61. Second mirror 63 further may be configured to reflect visible light beam 42 and tunable IR beam 52 and also to pivot about a second axis 64 that is perpendicular, or at least substantially perpendicular, to first axis 62. Thus, second mirror 63 may scan visible light beam 42 and tunable IR beam 52 across scanned surface 32 in a second direction, which may be perpendicular, or at least substantially perpendicular, to the first direction. Stated another way, the combination of first mirror 61 and second mirror 63 may permit visible light beam 42 and tunable IR beam 52 to be scanned across scanned surface 32 in two dimensions and/or to produce and/or generate a two-dimensional image, or map, of scanned surface 32.

As additional examples, scanning structure 60 may be configured to concurrently move both visible light beam 42 and tunable IR beam 52 relative to scanned surface 32, to operatively translate sample holder 20 relative to both visible light beam 42 and tunable IR beam 52, to move visible light source 40 independently of tunable IR source 50, and/or to move tunable IR source 50 independently of visible light source 40. Such a configuration may permit scanning structure 60 to scan visible light beam 42 and tunable IR beam 52 across scanned surface 32 while maintaining visible light beam 42 and tunable IR beam 52 coincident upon scanned surface 32.

Light filter 70 may include any suitable structure that may be adapted, configured, designed, and/or constructed to receive emitted light beam 38, to filter emitted light beam 38 to generate filtered light beam 72, to provide filtered light beam 72 to light detection system 80, and/or to selectively regulate a portion of emitted light beam 38 that is received by light detection system 80 as filtered light beam 72. As examples, light filter 70 may include one or more of a color filter, a wavelength discriminator, and/or a polarization selector. Light filter 70 may be utilized to selectively permit emitted light beam 38, which includes the sum frequency signal between visible light beam 42 and tunable IR beam 52 to enter light detection system 80. Light filter 70 also may be utilized to selectively attenuate portions of visible light beam 42 and/or tunable IR beam 52, which are reflected from scanned surface 32, such that these portions of visible light beam 42 and/or tunable IR beam 52 do not enter light detection system 80. Light filter 70 may be configured to increase a sensitivity of light detection system 80 for emitted light beam 38 and/or to increase a proportion of filtered light beam 72 that is defined by emitted light beam 38.

Light detection system 80 may include any suitable structure that may be adapted, configured, designed, and/or constructed to receive filtered light beam 72 and/or to quantify the at least one property of filtered light beam 72. As examples, light detection system 80 may be configured to detect one or more of an intensity of the filtered light beam, a wavelength of the filtered light beam, and/or a spectrum of the filtered light beam, with each of these properties of the filtered light beam potentially being utilized to provide imaging contrast within sampled location 34 of scanned surface 32. As another example, light detection system 80 may be configured for improved, or optimized detection at a frequency of emitted light beam 38 when relative to a frequency of visible light beam 42 and/or tunable IR beam 52. Examples of light detection system 80 include one or more of an optical detector 82, such as a low light level detection system, a photomultiplier, a photodiode, an avalanche photodiode, and/or a focal plane array.

It is within the scope of the present disclosure that light detection system 80 may detect the at least one property of filtered light beam 72 for, over, and/or across an entirety of sampled location 34. Stated another way light detection system 80 may detect a single value for each measured property of filtered light beam 72, such as the intensity of the filtered light beam, the wavelength of the filtered light beam, and/or the spectrum of the filtered light beam, for a given sampled location 34. Alternatively, it is also within the scope of the present disclosure that light detection system 80 may include a detection array. Such a detection array may be configured to detect a plurality of values of the at least one property of filtered light beam 72, with the plurality of values being detected as a function of location, or position, within sampled location 34.

Stated another way, light detection system 80 may be configured to detect a single, or bulk, property of filtered light beam 72, which is generated based upon an entirety of filtered light beam 72 that is received by light detection system 80 at a given point in time, thereby determining a single value for the property of filtered light beam 72 at the given point in time. Alternatively, light detection system 80 also may be configured to discretize and/or pixelate filtered light beam 72, thereby detecting positional information about the property of light beam 72 as a function of position within sampled location 34.

Alignment structure 80 may include any suitable structure that may be adapted, configured, designed, and/or constructed to operatively align visible light source 40, tunable IR source 50, sample holder 20, light detection system 80, and/or light filter 70. As an example, alignment structure 90 may be configured to operatively align visible light source 40, tunable IR source 50, sample holder 20, light detection system 80, and/or light filter 70 such that visible light beam 42 and tunable IR beam 52 are coincident upon sampled location 34, such that light filter 70 receives emitted light beam 38 from scanned surface 32, and/or such that light detection system 80 receives filtered light beam 72 from light filter 70. With this in mind, alignment structure 90 may include one or more components that may be operatively attached to, or may be configured to move, or align, visible light source 40, tunable IR source 50, sample holder 20, light detection system 80, and/or light filter 70, as illustrated in FIGS. 1-2.

As illustrated in dashed lines in FIGS. 1-2, systems 10 also may include a controller 96. Controller 96, when present, may be adapted, configured, designed, constructed, and/or programmed to control the operation of at least a portion of systems 10. This may include controlling the operation of systems 10 via and/or utilizing any suitable portion, subset, or step of any of methods 100, which are discussed in more detail herein.

As an example, controller 96 may control the operation of visible light source 40 and/or of visible light source control assembly 44 thereof. As another example, controller 96 may control the operation of tunable IR source 50 and/or of tunable IR source control assembly 54 thereof. As additional examples, controller 96 may control the operation of scanning structure 60, of light filter 70, of light detection system 80, and/or of alignment structure 90.

FIG. 4 is a flowchart depicting methods 100, according to the present disclosure, for imaging a scanned surface of a sample. Methods 100 include exposing a sampled location of the scanned surface to a visible light beam at 105 and may include selectively varying a property of the visible light beam at 110. Methods 100 also include exposing the sampled location to a tunable IR beam at 115 and may include selectively varying a property of the tunable IR beam at 120. Methods 100 further include varying a frequency of the tunable IR beam at 125 and inducing optical resonance within an imaged structure at 130. Methods 100 further may include filtering an emitted light beam with a light filter at 135 and include receiving a portion of the emitted light beam with a light detection system at 140 and scanning the visible light beam and the tunable IR beam across a scanned surface at 145. Methods 100 further may include oversampling the scanned surface at 150, such as by collecting a plurality, or sequence, of images of the scanned surface, and include generating an image at 155.

Exposing the sampled location to the visible light beam at 105 may include exposing the sampled location to any suitable visible light beam, such as visible light beam 42 of FIGS. 1-3. This may include directing the visible light beam onto, or incident upon, the sampled location of the scanned surface. This also may include directing the visible light beam from, or generating the visible light beam with, a visible light source, such as visible light source 40 of FIGS. 1-3.

Selectively varying the property of the visible light beam at 110 may include selectively varying any suitable property of the visible light beam in any suitable manner and/or utilizing any suitable structure. As examples, the selectively varying at 110 may include selectively varying one or more of an intensity of the visible light beam, a polarization of the visible light beam, a wavelength of the visible light beam, and/or a bandwidth of the visible light beam.

In general, and as discussed herein, the visible light beam will have a single, or fixed, wavelength, spectrum, bandwidth, polarization, and/or intensity during a remainder of methods 100 and/or at least during collection of a single image of the scanned surface. As such, the selectively varying at 110 may be performed prior to the exposing at 115, prior to the selectively varying at 120, prior to the varying at 125, prior to the inducing at 130, prior to the filtering at 135, prior to the receiving at 140, prior to the scanning at 145, prior to the oversampling at 150, and/or prior to the generating at 155.

Exposing the sampled location to the tunable IR beam at 115 may include exposing the sampled location to any suitable tunable IR beam, such as tunable IR beam 52 of FIGS. 1-3. This may include directing the tunable IR beam onto the sampled location of the scanned surface. This also may include directing the tunable IR beam from, or generating the tunable IR beam with, a tunable IR source, such as tunable IR source 50 of FIGS. 1-3.

Selectively varying the property of the tunable IR beam at 120 may include selectively varying any suitable property of the tunable IR beam in any suitable manner and/or utilizing any suitable structure. As examples, the selectively varying at 120 may include selectively varying one or more of an intensity of the tunable IR beam, a polarization of the tunable IR beam, a wavelength of the tunable IR beam, a frequency of the tunable IR beam, and/or a bandwidth of the tunable IR beam. It is within the scope of the present disclosure that the selectively varying at 120 may be included in, may form a portion of, and/or may be utilized to accomplish the tuning at 125, which is discussed in more detail herein.

Varying the frequency of the tunable IR beam at 125 may include varying the frequency of the tunable IR beam in any suitable manner. As an example, the varying at 125 may include tuning the tunable IR beam. As another example, the varying at 125 may include performing any suitable step discussed herein with reference to the selectively varying at 120. As another example, the varying at 125 may include varying the frequency of the tunable IR beam while concurrently performing the receiving at 140, such as to determine and/or detect a resonant frequency of the imaged structure. The varying at 125 also may be referred to herein as varying the wavelength of the tunable IR beam and/or as scanning a spectrum of the tunable IR beam.

Inducing the optical resonance within the imaged structure at 130 may include inducing the optical resonance within a portion of the imaged structure that extends at least partially within the sampled location of the scanned surface and may be responsive to, or a result of, the exposing at 115 and/or the varying at 125. Stated another way, the inducing at 130 may include inducing the optical resonance within a portion of the imaged structure upon which the visible light beam and the tunable IR beam are coincident. The resonant frequency for the imaged structure may be determined and/or induced based upon a frequency of the tunable IR beam that generates a maximum in an intensity of the portion of the emitted light beam that is received by the light detection structure during the receiving at 140. As used herein, the phrase "resonant frequency" may refer to a frequency of the tunable IR beam at which a resonant response is induced within the imaged structure. This resonant response may be induced because the frequency of the tunable IR beam corresponds to a material excitation, or an energy transition, within the imaged structure. When the frequency of the tunable IR beam matches the material excitation, or resonance, of the imaged structure, the tunable IR beam may be referred to herein as being "on-resonance" or as being at the "resonant frequency" of the material excitation.

Filtering the emitted light beam with the light filter at 135 may include filtering the emitted light beam to produce and/or generate the portion of the emitted light beam that is received by the light detection system during the receiving at 140. As an example, the filtering at 135 may include receiving the emitted light beam with a light filter and filtering the emitted light beam, with the light filter, to generate a filtered light beam. Under these conditions, the portion of the emitted light beam that is received during the receiving at 140 may include, or be, the filtered light beam.

The filtering at 135 may include filtering in any suitable manner. As examples, the filtering at 135 may include one or more of selecting a color of the filtered light beam, selecting a wavelength of the filtered light beam, selecting a wavelength range for the filtered light beam, and/or selecting a polarization of the filtered light beam. This may include filtering to attenuate frequencies outside the frequency range of the emitted light beam, or the sum frequency between the visible light beam and the tunable IR beam, thereby increasing the sensitivity of the light detection system to the emitted light beam. Receiving the portion of the emitted light beam with the light detection system at 140 may include receiving any suitable portion of the emitted light beam, from the sampled location of the scanned surface, that includes a sum frequency signal between the visible light beam and the tunable IR beam. This may include receiving the portion of the emitted light beam with, via, and/or utilizing any suitable light detection system, such light detection system 80 of FIGS. 1-3.

Scanning the visible light beam and the tunable IR beam across the scanned surface at 145 may include scanning both the visible light beam and the tunable IR beam across a scanned portion of the scanned surface. This may include performing the scanning at 145 while continuing at least the exposing at 105, the exposing at 115, and the receiving at 140. This also may include performing the scanning at 145 while maintaining the tunable IR beam at least partially coincident with the visible light beam. Stated another way, the scanning at 145 may include selectively varying a portion of the scanned surface, or of the scanned portion of the scanned surface, that defines the sampled location, thereby permitting one or more properties of the scanned surface to be mapped, or imaged, as a function of location on the scanned surface.

The scanning at 145 may be accomplished in any suitable manner and/or utilizing any suitable structure. As an example, the scanning at 145 may be performed utilizing a scanning structure, such as scanning structure 60 of FIGS. 1-3. As another example, the scanning at 145 may include concurrently moving both the visible light beam and the tunable IR beam relative to the scanned surface, operatively translating the sample holder relative to both the visible light beam and the tunable IR beam, moving the visible light source independently of the tunable IR source, and/or moving the tunable IR source independently of the visible light source. Stated another way, the scanning at 145 may include scanning in any suitable manner that maintains the visible light beam and the tunable IR beam coincident upon the scanned surface.

Oversampling the scanned surface at 150 may include collecting a plurality of images of the scanned portion of the scanned surface. The oversampling may permit and/or facilitate the generating at 155. As an example, and subsequent to the varying at 125, the oversampling at 150 may include repeating at least the receiving at 140 and the scanning at 145 while continuing the exposing at 105 and the exposing at 115. As another example, the oversampling at 150 may include collecting and/or generating a plurality of raw images of the scanned portion of the scanned surface. Under these conditions, each raw image may map the at least one property of the portion of the emitted light beam as a function of location within the scanned surface, and the plurality of raw images may be combined, during the generating at 155, to produce and/or generate a higher-resolution image of the scanned surface than what is represented in a single raw image of the scanned surface, such as by utilizing the selectively varying at 120 to select, highlight, and/or induce resonance in a different characteristic of, region of, and/or imaged structure within, the scanned portion of the scanned surface while continuing the exposing at 105 and the exposing at 115. As used herein, the phrase "raw image" may refer to an image that is generated by, or from, a single scan of the scanned surface.

Generating the image at 155 may include generating any suitable image of the scanned surface. The generating at 155 also may include generating based, at least in part, on the receiving at 140, the scanning at 145, and/or the oversampling at 150, and methods 100 also may include displaying the generated image.

The generating at 155 may include generating one or more images, with each image being representative of a different property of the portion of the emitted light beam that is received during the receiving at 140. As an example, each of the one or more images may correlate at least one property of the portion of the emitted light beam, which is received during the receiving at 140, to a location within the scanned portion of the scanned surface. Examples of property of the portion of the emitted light beam that may be represented in the one or more images include the frequency of the emitted light beam, the wavelength of the emitted light beam, the intensity of the emitted light beam, and/or the polarization of the emitted light beam.

It is within the scope of the present disclosure that the generating at 155 may include generating the image based upon a single scan of the scanned portion of the scanned surface. Alternatively, the generating at 155 also may include generating a super-resolution image of the scanned portion of the scanned surface and/or of an imaged structure that extends at least partially within the scanned portion of the scanned surface.

As an example, and when methods 100 include the oversampling at 150, the plurality of raw images may be combined to produce and/or generate the super-resolution image. As an example, and in each raw image, a location of the imaged structure, as represented in the raw image, may vary slightly, such as may be due to pixilation effects and/or to the limited resolution of the raw images. However, when the plurality of raw images is combined to generate the super-resolution image, an average size and/or location of the imaged structure may be quantified, thereby improving the resolution of the super-resolution image when compared to the raw images. Under these conditions, the optical resonance of the imaged structure, which is induced via the varying at 125, may be utilized to improve a signal-to-noise ratio of the raw images and/or to permit the imaged structure to be distinguished from a background, or noise.

The combination of the plurality of raw images may be accomplished in any suitable manner. As an example, deterministic methods may be utilized to combine the plurality of raw images and/or to generate the super-resolution image. Under these conditions, the deterministic algorithm formulates the combination of the plurality of raw images as a variational optimization problem. The objective function of the optimization problem may have two terms. The first may be a fidelity term, which models the image acquisition process. The second may be a regularization term, which dictates one or more assumptions about the super-resolution image.

As another example, stochastic methods may be utilized to combine the plurality of raw images and/or to generate the super-resolution image. Under these conditions, Bayesian inference may be utilized to estimate the super-resolution image by utilizing a Maximum a Posterior (MAP) estimate. To solve the MAP estimate, an optimization problem is formulated. The objective function of the optimization problem once again may have two terms. The first may be a likelihood function, which models the image acquisition process. The second may be the regularization term as discussed above. The likelihood function may represent the likelihood, or probability, that the imaged structure is within a certain portion of the imaged surface.

As a more specific but still illustrative, non-exclusive example, suppose a small defect was present on the surface that, due to a non-uniform molecular binding, changed the physical properties of the surface at that location. Such non-uniformities might only be 50 nm by 50 nm in size. The non-uniformity would lead to changes in the IR absorption spectrum, causing shifts in existing spectral features or new spectral features to appear. Surface sum-frequency generation (SSFG) might detect the presence of that non-uniformity, which could appear as a change in the spectrum when illuminated.

As used herein, SSFG includes mixing two input lasers, such as the visible light beam and the tunable IR beam disclosed herein, on a surface and/or at an interface. This mixing generates an output, such as the emitted light beam disclosed herein, at an output frequency that is the sum of the input frequencies of the two input lasers. The output frequency is mediated by the second order susceptibility tensor, which represents inherent material properties and/or responses of the object being imaged, such as the defect.

However, with conventional SSFG, there is no way to tell where, precisely, within the diffraction limited spot (which is, say, 1 micron in diameter) the non-uniformity occurs. This diffraction limitation is discussed in more detail herein. Thus, there also is no way to determine a size, a shape, an orientation, etc., of the non-uniformity. As a result, characterization of the non-uniformity would be qualitative and extremely vague, at best.

Application of the present super-resolution technique, including the associated statistical oversampling described above, will narrow the size, shape, orientation, and/or location of the non-uniformity. As an example, the statistical oversampling may permit positional information from a plurality of images to be combined, statistically combined, and/or statistically averaged to generate super-resolution images that illustrate the non-uniformity in a greater level of detail than would be possible via a single observation. This may permit more precise geometrical properties of the non-uniformity to be determined. As discussed herein, and unlike traditional super-resolution imaging, the surface sensing systems and methods disclosed herein may permit the higher resolution to be achieved without the addition of specialized fluorescent structures to the sample.

Illustrative, non-exclusive examples of inventive subject matter according to the present disclosure are described in the following enumerated paragraphs:

A1. A surface sensing system for imaging a scanned surface of a sample, the system comprising:

a sample holder including a support surface configured to support the sample;

a visible light source configured to direct a visible light beam incident upon a sampled location on the scanned surface when the sample is supported by the support surface;

a tunable infrared (IR) source configured to direct a tunable IR beam coincident with the visible light beam incident upon the sampled location on the scanned surface when the sample is supported by the support surface, optionally wherein the tunable IR source further is configured to selectively vary a wavelength of the tunable IR beam to permit the tunable IR beam to selectively induce resonance within an imaged structure that is positioned on the scanned surface;

a scanning structure configured to scan the visible light beam and the tunable IR beam across the scanned surface to selectively vary a portion of the scanned surface that defines the sampled location;

a light filter configured to receive an emitted light beam, which includes a sum frequency signal between the visible light beam and the tunable IR beam, from the scanned surface and to filter the emitted light beam to generate a filtered light beam, wherein the emitted light beam is emitted from the scanned surface responsive to both the visible light beam and the tunable IR beam being incident on the scanned surface;

a light detection system configured to receive the filtered light beam from the light filter; and an alignment structure configured to operatively align at least two of the visible light source, the tunable IR source, the sample holder, the light detection system, and the light filter.

A2. The system of paragraph A1, wherein the visible light beam has a fixed, or at least substantially fixed, wavelength.

A3. The system of any of paragraphs A1-A2, wherein the visible light beam has a fixed, or at least substantially fixed, spectrum.

A4. The system of any of paragraphs A1-A3, wherein the visible light source includes a pulsed laser system.

A5. The system of any of paragraphs A1-A4, wherein the visible light beam has a wavelength, a primary wavelength, or an average wavelength, of at least one of:

(i) at least 0.1 micrometer, at least 0.2 micrometers, at least 0.3 micrometers, at least 0.4 micrometers, at least 0.5 micrometers, or at least 0.6 micrometers; and (ii) at most 1 micrometer, at most 0.9 micrometers, at most 0.8 micrometers, at most 0.7 micrometers, at most 0.6 micrometers, or at most 0.5 micrometers.

A6. The system of any of paragraphs A1-A5, wherein the visible light source includes a solid state laser.

A7. The system of any of paragraphs A1-A6, wherein the visible light source includes a neodymium YAG laser.

A8. The system of paragraph A7, wherein the neodymium YAG laser is frequency doubled, optionally to a wavelength of 0.532 micrometers.

A9. The system of any of paragraphs A1-A8, wherein the visible light source includes a visible light source control assembly configured to selectively vary at least one of:

(i) an intensity of the visible light beam;

(ii) a polarization of the visible light beam;

(iii) a wavelength of the visible light beam; and (iv) a bandwidth of the visible light beam.

A10. The system of any of paragraphs A1-A9, wherein the tunable IR source has a selectively variable output wavelength.

A11. The system of any of paragraphs A1-A10, wherein the tunable IR source has a selectively variable output spectrum.

A12. The system of any of paragraphs A1-A11, wherein the tunable IR source includes an optical parametric oscillator.

A13. The system of any of paragraphs A1-A12, wherein the tunable IR source includes a lithium niobate ($LiNbO_3$) crystal laser.

A14. The system of any of paragraphs A1-A13, wherein the tunable IR source includes a tunable IR source control assembly configured to selectively vary at least one of:
(i) an intensity of the tunable IR beam;
(ii) a polarization of the tunable IR beam;
(iii) a wavelength of the tunable IR beam; and
(iv) a bandwidth of the tunable IR beam.

A15. The system of any of paragraphs A1-A14, wherein the scanning structure is configured to at least one of:
(i) concurrently move both the visible light beam and the tunable IR beam relative to the scanned surface;
(ii) operatively translate the sample holder relative to both the visible light beam and the tunable IR beam;
(iii) move the visible light source independently of the tunable IR source; and
(iv) move the IR source independently of the visible light source.

A16. The system of any of paragraphs A1-A15, wherein the scanning structure is a motorized scanning structure configured to selectively and automatically scan the visible light beam and the tunable IR beam across the scanned surface.

A17. The system of any of paragraphs A1-A16, wherein the scanning structure includes a sample holder translation structure configured to operatively translate the sample holder relative to both the visible light beam and the tunable IR beam.

A18. The system of any of paragraphs A1-A17, wherein the scanning structure includes:
(i) a first mirror configured to receive the visible light beam from the visible light source and to receive the tunable IR beam from the tunable IR source, wherein the first mirror further is configured to reflect the visible light beam and the tunable IR beam and to pivot about a first axis to scan the visible light beam and the tunable IR beam across the scanned surface in a first direction; and
(ii) a second mirror configured to receive the visible light beam and the tunable IR beam from the first mirror, wherein the second mirror is configured to reflect the visible light beam and the tunable IR beam and to pivot about a second axis, which is perpendicular, or at least substantially perpendicular, to the first axis, to scan the visible light beam and tunable IR beam across the scanned surface in a second direction that is perpendicular, or at least substantially perpendicular, to the first direction.

A19. The system of any of paragraphs A1-A18, wherein the scanning structure includes a optic steerer, optionally wherein the optic steerer includes at least one of an electrooptic steerer and an acoustooptic steerer.

A20. The system of any of paragraphs A1-A19, wherein the light detection system is a low light level detection system.

A21. The system of any of paragraphs A1-A20, wherein the light detection system includes an optical detector, optionally wherein the optical detector includes at least one of:
(i) a photomultiplier;
(ii) a photodiode;
(iii) an avalanche photodiode; and
(iv) a focal plane array.

A22. The system of any of paragraphs A1-A21, wherein the light detection system includes a detection array configured to detect at least one property of the filtered light stream as a function of a position within the sampled location.

A23. The system of any of paragraphs A1-A22, wherein the light detection system is configured to detect, or (the) at least one property of the filtered light stream includes, at least one of:
(i) an intensity of the filtered light beam;
(ii) a wavelength of the filtered light beam; and
(iii) a spectrum of the filtered light beam.

A24. The system of any of paragraphs A1-A23, wherein the light filter is configured to selectively regulate a portion of the emitted light beam that is received by the light detection system as the filtered light beam.

A25. The system of any of paragraphs A1-A24, wherein the light filter includes at least one of:
(i) a color filter;
(ii) a wavelength discriminator; and
(iii) a polarization selector.

A26. The system of any of paragraphs A1-A25, wherein the alignment structure is configured to operatively align the at least two of the visible light source, the tunable IR source, the sample holder, the light detection system, and the light filter such that:
(i) the visible light beam and the tunable IR beam are coincident upon the sampled location;
(ii) the light filter receives the emitted light beam from the scanned surface; and
(iii) the light detection system receives the filtered light beam from the light filter.

A27. The system of any of paragraphs A1-A26, wherein the system further includes a controller programmed to control the operation of at least a portion of the system.

A28. The system of paragraph A27, wherein the controller is programmed to control the system to perform any suitable portion of any of the methods of any of paragraphs B1-B18.

B1. A method for imaging a scanned surface of a sample, the method comprising:
exposing a sampled location of the scanned surface to a visible light beam;
exposing the sampled location of the scanned surface to a tunable infrared (IR) beam such that the tunable IR beam is at least partially coincident with the visible light beam;
varying a frequency of the tunable IR beam;
inducing optical resonance within an imaged structure that extends at least partially within the sampled location of the scanned surface;
receiving at least a portion of an emitted light beam, which includes a sum frequency signal between the visible light beam and the tunable IR beam, from the sampled location of the scanned surface with a light detection system;
scanning the visible light beam and the tunable IR beam across a scanned portion of the scanned surface while continuing at least the exposing the sampled location to the visible light beam, the exposing the sampled location to the tunable IR beam, and the receiving the emitted light beam and also while maintaining the tunable IR beam at least partially coincident with the visible light beam; and generating an image of the scanned portion of the scanned surface, wherein the generating is based, at least in part, on the receiving and on the scanning.

B2. The method of paragraph B1, wherein the method further includes oversampling the scanned portion of the scanned surface to facilitate the generating.

B3. The method of paragraph B2, wherein the oversampling includes repeating at least the receiving and the scanning, wherein the repeating is during the directing the visible light beam, during the directing the tunable IR beam, and subsequent to the tuning.

B4. The method of any of paragraphs B2-B3, wherein the oversampling includes generating a plurality of raw images of the scanned portion of the scanned surface, wherein each raw image in the plurality of raw images maps (the) at least one property of the portion of the emitted light beam as a function of location within the scanned portion of the scanned surface.

B5. The method of any of paragraphs B1-B4, wherein the exposing the sampled location to the visible light beam includes generating the visible light beam with a visible light source.

B6. The method of any of paragraphs B1-B5, wherein the method further includes selectively varying at least one of:
  (i) an intensity of the visible light beam;
  (ii) a polarization of the visible light beam;
  (iii) a wavelength of the visible light beam; and
  (iv) a bandwidth of the visible light beam.

B7. The method of any of paragraphs B1-B6, wherein the exposing the sampled location to the tunable IR beam includes generating the tunable IR beam with a tunable IR source.

B8. The method of any of paragraphs B1-B8, wherein the method further includes selectively varying at least one of:
  (i) an intensity of the tunable IR beam;
  (ii) a polarization of the tunable IR beam;
  (iii) a wavelength of the tunable IR beam; and
  (iv) a bandwidth of the tunable IR beam.

B9. The method of any of paragraphs B1-B8, wherein the varying the frequency of the tunable IR beam includes selectively varying the frequency of the tunable IR beam.

B10. The method of any of paragraphs B1-B9, wherein the varying the frequency of the tunable IR beam includes selectively varying the frequency of the tunable IR beam while concurrently performing the receiving to determine a resonant frequency for the imaged structure.

B11. The method of paragraph B10, wherein the resonant frequency for the imaged structure is determined based, at least in part, upon a frequency of the tunable IR beam that generates a maximum in an intensity of the portion of the emitted light beam that is received by the light detection system during the receiving.

B12. The method of any of paragraphs B1-B11, wherein the method further includes receiving the emitted light beam with a light filter and filtering the emitted light beam, with the light filter, to generate a filtered light beam, wherein the receiving at least the portion of the emitted light beam includes receiving the filtered light beam.

B13. The method of paragraph B12, wherein the filtering the emitted light beam includes at least one of:
  (i) selecting a color of the filtered light beam;
  (ii) selecting a wavelength of the filtered light beam; and
  (iii) selecting a wavelength range for the filtered light beam.

B14. The method of any of paragraphs B1-B13, wherein the scanning includes scanning to selectively vary a portion of the scanned surface that defines the sampled location.

B15. The method of any of paragraphs B1-B14, wherein the scanning includes scanning with a scanning structure.

B16. The method of any of paragraphs B1-B15, wherein the scanning includes at least one of:
  (i) concurrently moving both the visible light beam and the tunable IR beam relative to the scanned surface;
  (ii) operatively translating the sample holder relative to both the visible light beam and the tunable IR beam;
  (iii) moving the visible light source independently of the tunable IR source; and
  (iv) moving the IR source independently of the visible light source.

B17. The method of any of paragraphs B1-B16, wherein the generating the image of the scanned portion of the scanned surface includes correlating at least one property of the portion of the emitted light beam, which is received during the receiving, with a location within the scanned portion of the scanned surface.

B18. The method of paragraph B17, wherein the at least one property of the portion of the emitted light beam includes at least one of:
  (i) an intensity of the portion of the emitted light beam;
  (ii) a frequency of the portion of the emitted light beam; and
  (iii) a wavelength of the portion of the emitted light beam.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one example, to at least one, optionally including more than one, A, with no B present (and optionally including entities other than B); in another example, to at least one, optionally including more than one, B, with no A present (and optionally including entities other than A); in yet another example, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

The various disclosed elements of systems and steps of methods disclosed herein are not required to all systems and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

The invention claimed is:

1. A surface sensing system for imaging a scanned surface of a sample, the system comprising:
    a sample holder including a support surface configured to support the sample;
    a visible light source configured to direct a visible light beam incident upon a sampled location on the scanned surface when the sample is supported by the support surface;
    a tunable infrared (IR) source configured to direct a tunable IR beam coincident with the visible light beam incident upon the sampled location on the scanned surface when the sample is supported by the support surface, wherein the tunable IR source further is configured to selectively vary a wavelength of the tunable IR beam to permit the tunable IR beam to selectively induce resonance within an imaged structure that is positioned on the scanned surface;
    a scanning structure configured to scan the visible light beam and the tunable IR beam across the scanned surface to selectively vary a portion of the scanned surface that defines the sampled location, wherein the scanning structure is configured to at least one of:
        (i) concurrently move both the visible light beam and the tunable IR beam relative to the scanned surface;
        (ii) operatively translate the sample holder relative to both the visible light beam and the tunable IR beam;
        (iii) move the visible light source independently of the tunable IR source; and
        (iv) move the IR source independently of the visible light source;
    a light filter configured to receive an emitted light beam, which includes a sum frequency signal between the visible light beam and the tunable IR beam, from the scanned surface and to filter the emitted light beam to generate a filtered light beam, wherein the emitted light beam is emitted from the scanned surface responsive to both the visible light beam and the tunable IR beam being incident on the scanned surface;
    a light detection system configured to receive the filtered light beam from the light filter; and
    an alignment structure configured to operatively align at least two of:
        (i) the visible light source;
        (ii) the tunable IR source;
        (iii) the sample holder;
        (iv) the light detection system; and
        (v) the light filter.

2. The system of claim 1, wherein the visible light beam has an at least substantially fixed spectrum.

3. The system of claim 1, wherein the visible light source includes at least one of:
    (i) a pulsed laser system;
    (ii) a solid state laser; and
    (iii) a neodymium YAG laser, wherein the neodymium YAG laser is frequency doubled.

4. The system of claim 1, wherein the visible light beam has an average wavelength of at least 0.3 micrometers and at most 0.8 micrometers.

5. The system of claim 1, wherein the visible light source includes a visible light source control assembly configured to selectively vary at least one of:
    (i) an intensity of the visible light beam;
    (ii) a polarization of the visible light beam;
    (iii) a wavelength of the visible light beam; and
    (iv) a bandwidth of the visible light beam.

6. The system of any claim 1, wherein the tunable IR source has a selectively variable output spectrum.

7. The system of claim 1, wherein the tunable IR source includes at least one of:
    (i) an optical parametric oscillator; and
    a lithium niobate ($LiNbO_3$) crystal laser.

8. The system of claim 1, wherein the tunable IR source includes a tunable IR source control assembly configured to selectively vary at least one of:
    (i) an intensity of the tunable IR beam;
    (ii) a polarization of the tunable IR beam;
    (iii) a wavelength of the tunable IR beam; and
    (iv) a bandwidth of the tunable IR beam.

9. The system of claim 1, wherein the light detection system includes an optical detector, wherein the optical detector includes at least one of:
    (i) a photomultiplier;
    (ii) a photodiode;
    (iii) an avalanche photodiode; and
    (iv) a focal plane array.

10. The system of claim 1, wherein the light detection system is configured to detect at least one of:

(i) an intensity of the filtered light beam;
(ii) a wavelength of the filtered light beam; and
(iii) a spectrum of the filtered light beam.

11. The system of claim 1, wherein the light filter is configured to selectively regulate a portion of the emitted light beam that is received by the light detection system as the filtered light beam.

12. The system of claim 1, wherein the alignment structure is configured to operatively align such that:
   (i) the visible light beam and the tunable IR beam are coincident upon the sampled location;
   (ii) the light filter receives the emitted light beam from the scanned surface; and
   (iii) the light detection system receives the filtered light beam from the light filter.

13. The system of claim 1, wherein the system further includes a controller programmed to control the operation of at least a portion of the system.

* * * * *

UNITED STATES PATENT AND TRADEMARK OFFICE
CERTIFICATE OF CORRECTION

PATENT NO. : 10,274,310 B2
APPLICATION NO. : 15/388743
DATED : April 30, 2019
INVENTOR(S) : Jeffrey H. Hunt et al.

Page 1 of 1

It is certified that error appears in the above-identified patent and that said Letters Patent is hereby corrected as shown below:

In the Claims

Claim 6, Column 20, Line 44, delete "any".

Claim 7, Column 20, Line 49, add --(ii)-- to the beginning of the line.

Signed and Sealed this
Tenth Day of September, 2019

Andrei Iancu
*Director of the United States Patent and Trademark Office*